United States Patent
Ilmonen et al.

(10) Patent No.: US 12,329,742 B2
(45) Date of Patent: Jun. 17, 2025

(54) PHARMACEUTICAL COMPOSITION OF DAROLUTAMIDE

(71) Applicant: ORION CORPORATION, Espoo (FI)

(72) Inventors: Susanna Ilmonen, Espoo (FI); Juha Lintunen, Espoo (FI); Petteri Lyytinen, Espoo (FI); Marko Saalasti, Espoo (FI)

(73) Assignee: ORION CORPORATION, Espoo (FI)

( * ) Notice: Subject to any disclaimer, the term of this patent is extended or adjusted under 35 U.S.C. 154(b) by 681 days.

(21) Appl. No.: 17/623,922

(22) PCT Filed: Jul. 2, 2020

(86) PCT No.: PCT/FI2020/050478
§ 371 (c)(1),
(2) Date: Dec. 30, 2021

(87) PCT Pub. No.: WO2021/001603
PCT Pub. Date: Jan. 7, 2021

(65) Prior Publication Data
US 2022/0362216 A1    Nov. 17, 2022

(30) Foreign Application Priority Data
Jul. 2, 2019   (FI) .................................. 20195601

(51) Int. Cl.
*A61K 31/4155*   (2006.01)
*A61K 9/20*   (2006.01)
*A61K 9/28*   (2006.01)

(52) U.S. Cl.
CPC ........ *A61K 31/4155* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/28* (2013.01); *A61K 9/2813* (2013.01); *A61K 9/2826* (2013.01); *A61K 9/2853* (2013.01); *A61K 9/2866* (2013.01)

(58) Field of Classification Search
None
See application file for complete search history.

(56) References Cited

U.S. PATENT DOCUMENTS

2018/0064688 A1 *   3/2018   Dervan .............. A61K 31/4166

FOREIGN PATENT DOCUMENTS

WO   WO-2014128107 A1 *   8/2014   .......... A61K 31/517
WO   WO-2019032840 A1 *   2/2019   .......... A61K 31/4155

OTHER PUBLICATIONS

International Search Report of International Application No. PCT/FI2020/050478, mail date Oct. 13, 2020 (3 pages).

* cited by examiner

*Primary Examiner* — H. Sarah Park
(74) *Attorney, Agent, or Firm* — Finnegan, Henderson, Farabow, Garrett & Dunner, LLP

(57) ABSTRACT

The present invention relates to a pharmaceutical composition for oral administration, particularly in the form of a tablet, comprising darolutamide or a pharmaceutically acceptable salt thereof as an active ingredient. Darolutamide is a potent androgen receptor (AR) modulator useful in the treatment of cancer, particularly AR dependent cancer such as prostate cancer, and other diseases where AR antagonism is desired.

6 Claims, 1 Drawing Sheet

PHARMACEUTICAL COMPOSITION OF DAROLUTAMIDE

This is a National Stage Application under 35 U.S.C. § 371 of International Patent Application No. PCT/FI2020/050478, filed Jul. 2, 2020, which claims the benefit of priority of Finnish Patent Application No. 20195601, filed Jul. 2, 2019, both of which are incorporated herein by reference.

FIELD OF THE INVENTION

The present invention relates to a pharmaceutical composition for oral administration, particularly in the form of a tablet, comprising darolutamide or a pharmaceutically acceptable salt thereof as an active ingredient.

BACKGROUND OF THE INVENTION

Darolutamide or N—((S)-1-(3-(3-chloro-4-cyanophenyl)-1H-pyrazol-1-yl)-propan-2-yl)-5-(1-hydroxyethyl)-1H-pyrazole-3-carboxamide (I) and its chemical synthesis have been disclosed in International patent publications WO 2011/051540 and WO 2016/162604. Darolutamide is a potent androgen receptor (AR) modulator useful in the treatment of cancer, particularly AR dependent cancer such as prostate cancer, and other diseases where AR antagonism is desired. Darolutamide is represented by the structure:

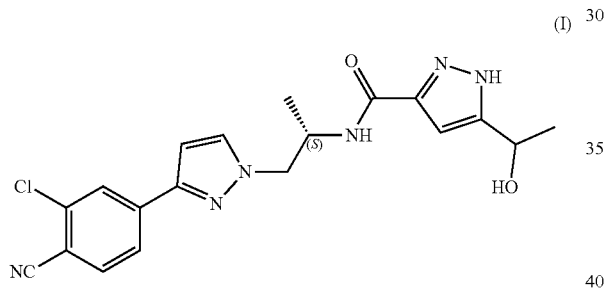

(I)

As the hydrogen atom of the pyrazole ring may exist in tautomeric equilibrium between the 1- and 2-position, it is recognized by the skilled person that the above structure and the chemical name "N—((S)-1-(3-(3-chloro-4-cyanophenyl)-1H-pyrazol-1-yl)-propan-2-yl)-5-(1-hydroxyethyl)-1H-pyrazole-3-carboxamide (I)," as referred to herein, is inclusive of the tautomer of compound (I), namely N—((S)-1-(3-(3-chloro-4-cyanophenyl)-1H-pyrazol-1-yl)-propan-2-yl)-3-(1-hydroxyethyl)-1H-pyrazole-5-carboxamide.

Polymorphic crystalline form I of darolutamide has been disclosed in WO 2016/120530. Crystalline particles of darolutamide having specific surface area (SSA) in the range of 8-16 $m^2/g$ has been disclosed in WO 2018/162793.

Darolutamide is poorly soluble in water. Oral administration of poorly soluble active ingredients is often problematic. An oral dosage form, such as a tablet, should provide the release of substantially all of the active ingredient and provide sufficient dissolution properties. While providing suitable release and dissolution of the active ingredient, the formulation should also have properties which enables the manufacture of the dosage form in industrial scale.

SUMMARY OF THE INVENTION

The present invention provides a pharmaceutical composition for oral administration, particularly in the form of a tablet, comprising darolutamide or a pharmaceutically acceptable salt thereof as an active ingredient. The composition provides efficient release of darolutamide and constant dissolution properties producing effective and reproducible in vivo plasma concentrations. At the same time, the composition provides excellent tabletability of the tableting mass, good resistance to crushing and low brittleness enabling manufacture of the tablets in large industrial scale. The composition is robust against variations in the manufacturing process during operation and technical transfer such that the properties of the composition are not affected. Moreover, the composition enables high drug loads which is desirable in respect of patient compliance. Therefore, the composition according to the invention is particularly suitable as a dosage form for the treatment of patients suffering from androgen receptor dependent diseases such as prostate cancer.

Thus, according to one embodiment, the present invention provides a pharmaceutical composition comprising (a) at least 35%, preferably at least 40%, per weight of the composition, of darolutamide or a pharmaceutically acceptable salt thereof; (b) 5-60%, per weight of the composition, of a filler; (c) 0.5-10%, per weight of the composition, of a disintegrant; (d) 0.5-10%, per weight of the composition, of a binder; and (e) 0.2-5%, per weight of the composition, of a lubricant.

DETAILED DESCRIPTION OF THE INVENTION

Figure 1:
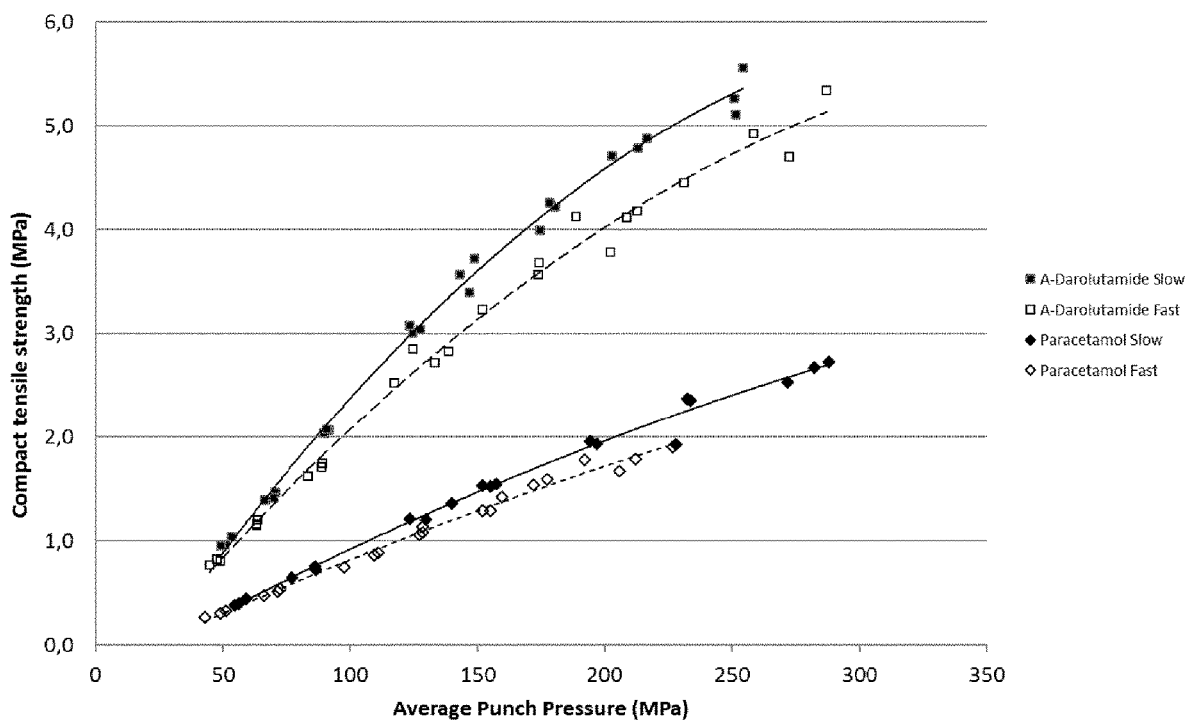
FIG. 1 compares the average punch pressure vs. tensile strength curve of "A-Darolutamide" composition with the curve of "Paracetamol" composition using slow or fast compression speed.

The present invention relates to a pharmaceutical composition for oral administration, particularly in the form of a tablet, comprising darolutamide or a pharmaceutically acceptable salt thereof as an active ingredient. The term "darolutamide or a pharmaceutically acceptable salt thereof" is inclusive of a solvent, tautomer or cocrystal form of darolutamide or a pharmaceutically acceptable salt thereof. Darolutamide or a pharmaceutically acceptable salt thereof may be in amorphous or crystalline including microcrystalline state. Preferred form is crystalline form I of darolutamide as described in WO 2016/120530. It may be characterized by a X-ray powder diffraction pattern comprising characteristic peaks at about 8.5, 10.4, 16.6, 16.9, and 24.3 degrees 2-theta (Cu filled X-ray tube at room temperature). Preferably, said crystalline form I may be characterized by a X-ray powder diffraction pattern comprising characteristic peaks at about 6.4, 8.5, 9.6, 9.7, 10.4, 12.8, 13.6, 14.9, 15.9, 16.6, 16.9, 18.7, 19.2, 21.8, 24.3, and 25.5 degrees 2-theta (Cu filled X-ray tube at room temperature).

In accordance with one embodiment of the present invention, there is provided pharmaceutical composition comprising (a) at least 35%, preferably at least 40%, per weight of the composition, of darolutamide or a pharmaceutically acceptable salt thereof; (b) 5-60%, per weight of the composition, of a filler; (c) 0.5-10%, per weight of the composition, of a disintegrant; (d) 0.5-10%, per weight of the composition, of a binder; and (e) 0.2-5%, per weight of the composition, of a lubricant.

In a subclass of the above embodiment are compositions which comprise 40-85%, preferably 45-80%, for example 45-75%, 45-70%, 45-65%, 45-60% or 45-55%, per weight of the composition, of darolutamide or a pharmaceutically acceptable salt thereof.

In a subclass of any of the above embodiments are compositions comprising 5-55%, preferably 5-50%, for example 5-45% or 25-50%, per weight of the composition, of a filler.

As used herein, a "filler" refers to one or more pharmaceutically acceptable excipient(s) that adds bulkiness to a pharmaceutical composition. Examples of fillers include lactose, calcium hydrogen phosphate, microcrystalline cellulose, sorbitol, starches, sugars (e.g., mannitol or sucrose) or any combination thereof. According to one preferred embodiment, the filler comprises calcium hydrogen phosphate. The term "calcium hydrogen phosphate", as used herein, includes anhydrous calcium hydrogen phosphate and hydrates such as calcium hydrogen phosphate dihydrate. Anhydrous calcium hydrogen phosphate is preferred.

According to another preferred embodiment, the filler comprises calcium hydrogen phosphate in combination with lactose and/or microcrystalline cellulose. According to one particularly preferred embodiment, the filler comprises a combination of calcium hydrogen phosphate and lactose. According to one embodiment, the filler consists of a combination of calcium hydrogen phosphate and lactose. The term "lactose", as used herein, includes lactose monohydrate and anhydrous lactose. Lactose monohydrate is preferred.

In a subclass of any of the above embodiments are compositions comprising 5-20%, for example 7-15%, per weight of the composition, of calcium hydrogen phosphate. In another subclass of any of the above embodiments are compositions comprising 5-20%, for example 7-15%, per weight of the composition, of calcium hydrogen phosphate and 10-40%, for example 15-40%, 20-40% or 25-35%, per weight of the composition, of lactose.

In a subclass of any of the above embodiments are compositions comprising 0.5-8%, preferably 3-7%, per weight of the composition, of a disintegrant.

As used herein, a "disintegrant" refers to one or more pharmaceutically acceptable excipient(s) which is added to the pharmaceutical composition to cause its disintegration to support the release of the active ingredient from the pharmaceutical composition. Examples of disintegrants include croscarmellose sodium, cross-linked polyvinylpyrollidone, sodium starch glycolate or any combination thereof.

According to one preferred embodiment, the disintegrant comprises croscarmellose sodium.

In a subclass of any of the above embodiments are compositions comprising 0.5-8%, preferably 3-7%, per weight of the composition, of a binder.

As used herein, a "binder" refers to one or more pharmaceutically acceptable excipient(s) that imparts enhanced cohesion by binding the active ingredient and the excipients together in a mixture. Examples of binders include polyvinyl pyrrolidone (PVP), polyvinyl acetate, polyvinyl alcohol, hydroxypropylcellulose (HPC), hydroxypropylmethylcellulose (HPMC) and combinations thereof.

According to one preferred embodiment, the binder comprises polyvinylpyrrolidone (PVP).

In a subclass of any of the above embodiments are compositions comprising 0.2-3%, preferably 0.3-2%, for example 0.5-2%, per weight of the composition, of a lubricant.

As used herein, a "lubricant" refers to one or more pharmaceutically acceptable excipient(s), which is added to the pharmaceutical composition to reduce friction, heat, and wear when introduced between solid surfaces. Examples of lubricants include magnesium stearate, stearic acid, talc, silica, calcium stearate, canauba wax, sodium stearyl funarate, and combinations thereof.

According to one preferred embodiment, the lubricant comprises magnesium stearate.

According to still another embodiment, the composition comprises (a) at least 35%, preferably at least 40%, for example 45-80%, per weight of the composition, of darolutamide or a pharmaceutically acceptable salt thereof; (b) 5-20%, per weight of the composition, of calcium hydrogen phosphate; (c) 0.5-10%, per weight of the composition, of a disintegrant; (d) 0.5-10%, per weight of the composition, of a binder; and (e) 0.2-5%, per weight of the composition, of a lubricant.

According to still another embodiment, the composition comprises (a) at least 35%, preferably at least 40%, for example 45-80%, per weight of the composition, of darolutamide or a pharmaceutically acceptable salt thereof; (b) 5-20%, per weight of the composition, of calcium hydrogen phosphate; (c) 10-40%, per weight of the composition, of lactose; (d) 0.5-10%, per weight of the composition, of a disintegrant; (e) 0.5-10%, per weight of the composition, of a binder; and (f) 0.2-5%, per weight of the composition, of a lubricant.

According to still another embodiment, the composition comprises (a) 45-80%, per weight of the composition, of darolutamide or a pharmaceutically acceptable salt thereof; (b) 5-20%, per weight of the composition, of calcium hydrogen phosphate; (c) 10-40%, per weight of the composition, of lactose (d) 0.5-10%, per weight of the composition, of croscarmellose sodium; (e) 0.5-10%, per weight of the composition, of polyvinylpyrrolidone; and (f) 0.2-5%, per weight of the composition, of magnesium stearate.

In a subclass of the above embodiment are compositions, which comprise 45-75%, 45-70%, 45-65%, 45-60% or 45-55%, per weight of the composition, of darolutamide or a pharmaceutically acceptable salt thereof.

The pharmaceutical composition of the invention can be, for example, in the form of granules, pellets, capsules or tablets. Such compositions can be prepared, for example, by wet granulation, dry granulation or dry compression. In a preferred embodiment, the pharmaceutical composition of the invention is in the form of a coated or uncoated tablet. According to one preferred embodiment, the tablet is prepared by wet granulation.

According to one embodiment, the tablet comprises an intragranular part and an extragranular part. According to still another embodiment, the intragranular part comprises darolutamide or a pharmaceutically acceptable salt thereof, the filler, the binder and a portion of the disintegrant, and the extragranular part comprises the lubricant and the rest of the disintegrant.

In accordance with one embodiment of the invention the process for manufacturing a pharmaceutical composition of the invention is characterized by the steps of (a) mixing darolutamide or a pharmaceutically acceptable salt thereof, filler, binder and a first portion of the disintegrant; (b) granulating the mixture using water as granulation liquid; (c) drying the wet granules; (d) mixing lubricant and the rest of the disintegrant with the granules; (e) compressing the resulting mass into tablets; and, optionally, coating the tablet with one or further pharmaceutically acceptable film-coating agent.

For the manufacture of the pharmaceutical composition, darolutamide, preferably in its non-salt form and in crystalline form I, is suitably milled to the particle size having the volume median diameter (Dv50) generally not more than 200 μm, preferably not more than 150 μm, more preferably not more than 100 μm, for example in the range of 10-100 μm, more typically between 15-95 μm, for example, between 20-90 μm. The particle size distribution can be analyzed by laser light diffraction, for example using Beckman Coulter LS13320 laser diffraction particle size analyzer equipped with Tornado Dry Powder System using air as dispersion medium with measurement pressure 24"$H_2O$±2"$H_2O$, sample amount 10 ml, system controlled target 5% for obscuration and applying Fraunhofer optical model.

Milling of the active ingredient can be carried out using suitable feeder and milling equipment, for example, single or twin screw/auger feeders, hammer mills, pin mills, jet mills or sieve mills, using suitable rotor speeds such as, for example 3000-10000 rpm. The milling can be conducted in a suitable temperature, for example, in room temperature or lower.

The composition of the invention can be suitably manufactured, for example, by first mixing darolutamide or a pharmaceutically acceptable salt thereof, filler, binder and a first portion of the disintegrant (for example 20-80 w-% of the total) in a suitable granulator vessel, for example wet high shear granulator. The mixture is then suitably granulated in the granulator using purified water as granulating liquid. The wet granules can then be screened, for example, using a screening mill unit (rotating impeller) and subsequently dried, for example, in a fluid bed dryer.

The dried granules may then be screened with a screening apparatus, for example a screening mill. Thereafter, the rest of the disintegrant can be added to the granules followed by blending the mixture in, for example, a diffusion mixer. Lubricant is then added to the mass of the previous step followed by blending. The tablet mass is then compressed into tablet cores, for example, in a power assisted rotary tablet press.

The tablet cores can be provided with a water soluble film coating, if desired, to facilitate tablet swallowing, to protect from direct contact with the drug substance and to improve aesthetics. Suitable film coating agents can be selected from the group of plasticizers, film-forming agents and colorants. Optionally an anti-tacking agent or opacifier can be used. The plasticizer, such as polyethylene glycol (PEG), the film-forming agent, such as hydroxypropylmethyl cellulose (HPMC), and the colorants, such as ferric oxide and titanium dioxide, are combined with film-coating liquids, preferably water, to result in a homogeneous coating suspension which is brought up, preferably sprayed, on the tablets in a suitable coating device, such as for example a perforated drum coater.

In accordance with one embodiment of the invention, the pharmaceutical composition of the invention is an immediate release dosage form, preferably a tablet. Preferred are compositions, which provide a dissolution of at least 80% of darolutamide or a pharmaceutically acceptable salt thereof after 60 minutes in 0.01 M hydrochloric acid with 1.0% of sodium lauryl sulfate using paddle apparatus (USP apparatus 2) with paddle speed of 75 rpm at room temperature.

Darolutamide or a pharmaceutically acceptable salt thereof is suitably administered, for example for the treatment of prostate cancer, in an amount ranging from about 100 mg to about 3000 mg, preferably from about 300 mg to about 2500 mg, more preferably from about 500 mg to about 2000 mg, for example from about 800 mg to about 1500 mg, such as about 1200 mg, per day to the patient. A patient is a mammal, particularly a human, in need of treatment for, for example, prostate cancer. The dose can be administered once daily or divided to several times a day, for example twice daily. The composition of the invention, such as a tablet, may comprise darolutamide or a pharmaceutically acceptable salt thereof in an amount ranging from about 50 mg to about 1000 mg, preferably from about 100 mg to about 800 mg, more preferably from about 150 mg to about 600 mg, for example from about 200 mg to about 400 mg, such as 300 mg. Such composition can be administered once or several times a day, for example one tablet or several tablets once, twice or several times daily such as two 300 mg tablets twice daily.

The invention is further illustrated by the following examples.

Example 1. Immediate Release Tablet of Darolutamide

| Composition | Amount (mg) |
|---|---|
| Drug substance | |
| Darolutamide milled | 300.0 |
| Tablet core | |
| Calcium hydrogen phosphate (anhydrous) | 60.2 |
| Croscarmellose sodium | 30.0 |
| Lactose monohydrate | 180.4 |
| Magnesium stearate | 5.4 |
| Polyvinylpyrrolidone | 24.0 |
| Purified water [a] | — |
| Weight (uncoated tablet) | 600.0 |
| Film coating [b] | 18 |
| Purified water [a] | — |
| Weight (coated tablet) | 618 |

[a] Water is used and quantitatively removed during the manufacturing process
[b] Contains HPMC, lactose monohydrate, PEG and titanium dioxide

Example 2. Immediate Release Tablet of Darolutamide

| Composition | Amount (mg) |
|---|---|
| Drug substance | |
| Darolutamide milled | 480.4 |
| Tablet core | |
| Calcium hydrogen phosphate (anhydrous) | 60.2 |
| Croscarmellose sodium | 30.0 |
| Magnesium stearate | 5.4 |
| Polyvinylpyrrolidone | 24.0 |
| Purified water [a] | — |
| Weight (uncoated tablet) | 600.0 |
| Film coating [b] | 18 |
| Purified water [a] | — |
| Weight (coated tablet) | 618 |

[a] Water is used and quantitatively removed during the manufacturing process
[b] Contains HPMC, lactose monohydrate, PEG and titanium dioxide Example 3. Immediate Release Tablet of Darolutamide

| Composition | Amount (mg) |
|---|---|
| Drug substance | |
| Darolutamide milled | 240.0 |
| Tablet core | |
| Calcium hydrogen phosphate (anhydrous) | 75.2 |
| Croscarmellose sodium | 30.0 |
| Lactose monohydrate | 225.4 |
| Magnesium stearate | 5.4 |
| Polyvinylpyrrolidone | 24.0 |
| Purified water [a] | — |
| Weight (uncoated tablet) | 600.0 |
| Film coating [b] | 18 |
| Purified water [a] | — |
| Weight (coated tablet) | 618 |

[a] Water is used and quantitatively removed during the manufacturing process
[b] Contains HPMC, lactose monohydrate, PEG and titanium dioxide Example 4. Immediate Release Tablet of Darolutamide

| Composition | Amount (mg) |
|---|---|
| Drug substance | |
| Darolutamide milled | 300.0 |
| Tablet core | |
| Calcium hydrogen phosphate (anhydrous) | 59.5 |
| Croscarmellose sodium | 48.0 |
| Lactose monohydrate | 178.1 |
| Magnesium stearate | 2.4 |
| Polyvinylpyrrolidone | 12.0 |
| Purified water [a] | — |
| Weight (uncoated tablet) | 600.0 |
| Film coating [b] | 18 |
| Purified water [a] | — |
| Weight (coated tablet) | 618 |

[a] Water is used and quantitatively removed during the manufacturing process
[b] Contains HPMC, lactose monohydrate, PEG and titanium dioxide Example 5. Immediate Release Tablet of Darolutamide

| Composition | Amount (mg) |
|---|---|
| Drug substance | |
| Darolutamide milled | 300.0 |
| Tablet core | |
| Calcium hydrogen phosphate (anhydrous) | 61.8 |
| Croscarmellose sodium | 6.0 |
| Lactose monohydrate | 184.2 |
| Magnesium stearate | 12.0 |
| Polyvinylpyrrolidone | 36.0 |
| Purified water [a] | — |
| Weight (uncoated tablet) | 600.0 |
| Film coating [b] | 18 |
| Purified water [a] | — |
| Weight (coated tablet) | 618 |

[a] Water is used and quantitatively removed during the manufacturing process
[b] Contains HPMC, lactose monohydrate, PEG and titanium dioxide The tablet compositions of Examples 1 to 5 are prepared by mixing the drug substance, lactose monohydrate, polyvinylpyrrolidone, anhydrous calcium hydrogen phosphate and a portion of croscarmellose sodium in a high-shear granulator. The mixture is granulated by spraying water is into the mixture. The granules are dried in a fluid bed dryer. Rest of the croscarmellose sodium is mixed with the granules. Magnesium stearate is then added followed by mixing. The obtained mixture is compressed into tablets with a tablet press. Water is combined with the mixture of coating excipients to prepare a coating suspension. Finally, the tablets are coated by spraying the coating suspension on the tablet cores in a heated pan coater until the theoretical weight gain in tablets is reached.

Example 6. Comparative Study of Tabletability Properties

A first mass for tableting was manufactured according to Example 1 (the "A-Darolutamide" composition). The same was repeated but using paracetamol as a model drug instead of darolutamide (the 'Paracetamol' composition). A third mass was manufactured according to Example 1 but replacing lactose monohydrate by microcrystalline cellulose (the "B-Darolutamide" composition). The actual compositions manufactured are presented below in Table 1.

TABLE 1

Compositions manufactured for the comparative study

| Ingredients | A-Darolutamide | Amount (mg) Paracetamol | B-Darolutamide |
|---|---|---|---|
| Drug substance | | | |
| Darolutamide milled | 300.0 | — | 300.0 |
| Paracetamol | — | 300.0 | — |
| Tablet core | | | |
| Calcium hydrogen phosphate (anhydrous) | 60.2 | 60.2 | 60.2 |
| Croscarmellose sodium | 30.0 | 30.0 | 30.0 |
| Lactose monohydrate | 180.4 | 180.4 | — |
| Microcrystalline cellulose | — | — | 180.4 |
| Magnesium stearate | 5.4 | 5.4 | 5.4 |
| Polyvinyl pyrrolidone | 24.0 | 24.0 | 24.0 |
| Purified water [a] | — | — | — |
| Tablet weight | 600.0 | 600.0 | 600.0 |

[a] Water is used and quantitatively removed during the manufacturing process

Tablets were compressed on a single punch hydraulic press with a 10 mm round tooling to approximately 300 mg unit weight and to a minimum of 7 different compression heights. A single ended sine wave profile was used with a target 10 ms dwell time for fast compression and a single ended sine wave profile with a target 100 ms dwell time for a slow compression. Tablet diameter, height and resistance to crushing were determined by caliper and hardness tester, respectively.

Average force of compression was determined as a mean of upper and lower punch peak force and converted to pressure by dividing by the punch tip area. Tensile strength was determined using equation:

$$\text{Tensile strength} = 2P/(\pi \cdot D \cdot t)$$

where
$P$ = resistance to crushing
$\pi$ = mathematical constant pi
$D$ = tablet diameter
$t$ = tablet thickness FIG. 1 shows the average punch pressure vs. tensile strength curves for "A-Darolutamide" and "Paracetamol" compositions with slow or fast compression speed.

Tabletability profile presented in FIG. 1 demonstrates clearly that the tableting mass of Example 1 ("A-Darolutamide") is exceptionally suitable for darolutamide tableting process with slow and fast compression speed. Comparison to a similar composition but having a model drug (paracetamol) as an active ingredient shows that the same composition used with another drug substance did not produce tablets with acceptable tensile strength within compression force range appropriate for tablet production.

Figure 2:
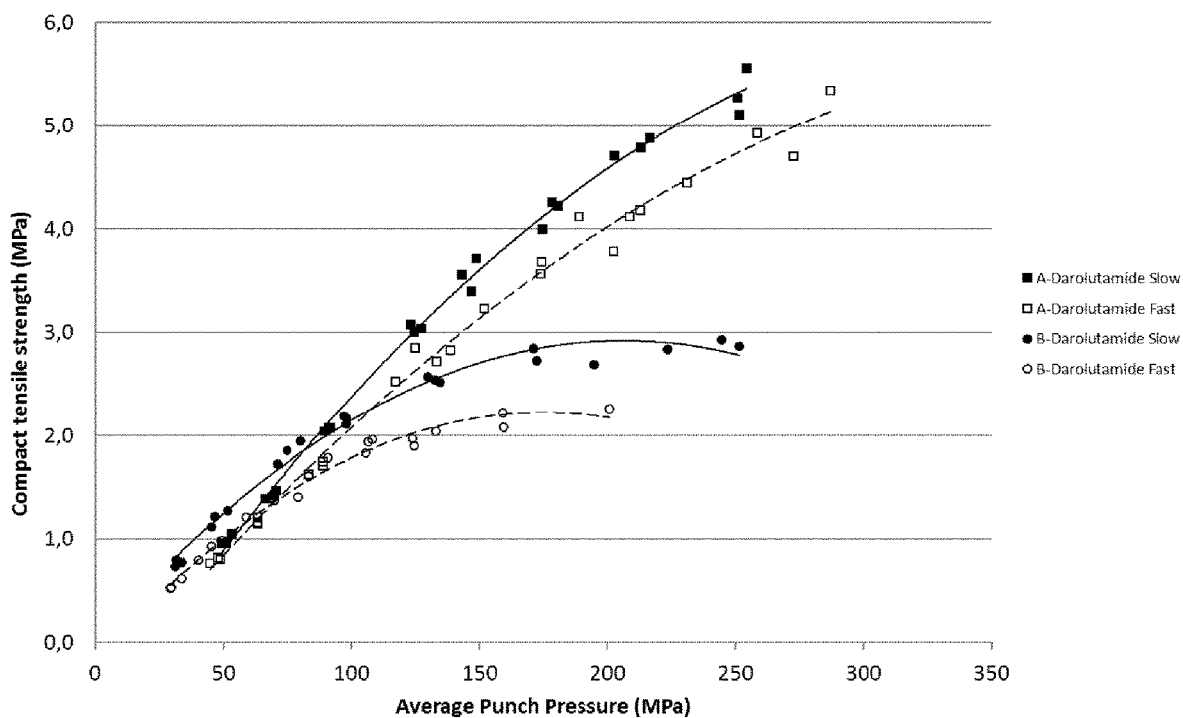
FIG. 2 compares the average punch pressure vs. tensile strength curve of "A-Darolutamide" composition with the curve of "B-Darolutamide" composition using slow or fast compression speed.

FIG. 2 compares the average punch pressure vs. tensile strength curve of "A-Darolutamide" composition with the curve of "B-Darolutamide" composition in which lactose was replaced by microcrystalline cellulose. Surprisingly, the composition containing microcrystalline cellulose did not show improved tabletability properties. Instead, particularly upon fast compression this composition poses a risk for tablet production due to insufficient tensile strength.

The invention claimed is:

1. A pharmaceutical composition comprising
   (a) at least 45-80%, per weight of the composition, of darolutamide or a pharmaceutically acceptable salt thereof;
   (b) 7-20%, per weight of the composition, of calcium hydrogen phosphate;
   (c) 25-35%, per weight of the composition, of lactose;
   (d) 0.5-10%, per weight of the composition, of a disintegrant;
   (e) 0.5-10%, per weight of the composition, of a binder; and
   (f) 0.2-5%, per weight of the composition, of a lubricant;
   wherein the composition is in the form of a tablet.

2. The pharmaceutical composition according to claim 1, wherein the disintegrant is croscarmellose sodium; the binder is polyvinylpyrrolidone; and the lubricant is magnesium stearate.

3. The pharmaceutical composition according to claim 1, wherein darolutamide or a pharmaceutically acceptable salt thereof is present in an amount of 300 mg or 600 mg.

4. The pharmaceutical composition according to claim 2, wherein darolutamide or a pharmaceutically acceptable salt thereof is present in an amount of 300 mg or 600 mg.

5. The pharmaceutical composition according to claim 2, comprising a tablet core and a film coating, wherein the tablet core comprises:
   (a) about 300 mg of darolutamide or a pharmaceutically acceptable salt thereof;
   (b) about 60 mg of calcium hydrogen phosphate;
   (c) about 180 mg of lactose monohydrate;
   (d) about 30 mg of croscarmellose sodium;
   (e) about 24 mg of polyvinylpyrrolidone; and
   (f) about 5.4 of magnesium stearate.

6. The pharmaceutical composition according to claim 1, wherein darolutamide or a pharmaceutically acceptable salt thereof is in a crystalline form.

* * * * *

UNITED STATES PATENT AND TRADEMARK OFFICE
CERTIFICATE OF CORRECTION

| | | |
|---|---|---|
| PATENT NO. | : 12,329,742 B2 | Page 1 of 1 |
| APPLICATION NO. | : 17/623922 | |
| DATED | : June 17, 2025 | |
| INVENTOR(S) | : Ilmonen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 715 days.

Signed and Sealed this
Sixteenth Day of December, 2025

John A. Squires
*Director of the United States Patent and Trademark Office*